(12) United States Patent
Singh et al.

(10) Patent No.: US 6,440,056 B1
(45) Date of Patent: Aug. 27, 2002

(54) DIACETYLENICS CONTAINING ADJACENT TRIPLE BONDS

(75) Inventors: Alok Singh, Springfield; Paul Schoen, Alexandria, both of VA (US); Dan Zabetakis, College Park, MD (US); Joel M. Schnur, Burke, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/845,106

(22) Filed: Apr. 27, 2001

(51) Int. Cl.$^7$ .................................................. C11B 3/00
(52) U.S. Cl. ...................................................... 584/165
(58) Field of Search ......................................... 584/165

(56) References Cited

U.S. PATENT DOCUMENTS 4,867,917 A  *  9/1989  Schmur

* cited by examiner

*Primary Examiner*—Deborah D. Carr
(74) *Attorney, Agent, or Firm*—John J. Karasek; George A. Kap

(57) ABSTRACT

This invention pertains to a process for preparing diacetylenics, to diacetylenic compounds and to reduced diacetylenic compounds. The process includes the steps of reacting coupling an acetylenic acid in presence of cupric chloride in Ethylamine and hydroxylamine hydrochloride to form a diacetylenic diacid; reacting the diacetylenic diacid with a lithium compound, trimethylsilyl chloride and hydrochloric acid to form a diacetylenic compound; and reducing the diacetylenic compound to a reduced diacetylenic compound. The diacetylenic compounds have the formula $COOH-(CH_2)_m-C{\equiv}C-C{\equiv}C-(CH_2)_m-C(=O)-R$ or $R-C(=O)-(CH_2)_m-C{\equiv}C-C{\equiv}C-(CH_2)_m-C(=O)-R$ and the reduced cyclic diacetylenic compounds have the formula $COOH-(CH_2)_m-C{\equiv}C-C{\equiv}C-(CH_2)_m-CH_2-R$ or $R-CH_2-(CH_2)_m-C{\equiv}C-C{\equiv}C-(CH_2)_m-CH_2-R$, where m is 1–18 and R is selected from alkyl groups of 1–10 and cyclic groups containing 6–35 carbon atoms and aryl moieties

20 Claims, No Drawings

DIACETYLENICS CONTAINING ADJACENT TRIPLE BONDS

BACKGROUND OF THE INVENTION

1. Field of the Invention

This invention pertains to a process for preparing diacetylenics, to diacetylenic compounds and to reduced diacetylenic compounds.

2. Description of Related Art

Diacetylenic acids are a major precursor for making diacetylenic phospholipids, which are basic building materials for making and stabilizing technologically useful structures called "tubules". The high cost of the diacetylenic acids pushes the cost of phospholipids up thus making them less attractive in the development of technologies such as electronic devices; controlled release of substances, particularly drugs; drug delivery systems; nano composites; and the like. Diacetylenic phospholipids consisting of diacetylenic acids with keto functional groups, and a combination of keto and aryl or cyclic groups, constitutes useful molecular probes for studying bilayer membrane structures and dynamics.

The prior art process of making the isomeric diacetylenic acids, disclosed in U.S. Pat. No. 4,867,917, involves a heterocoupling reaction between a starting acetylenic acid and an omega haloalkyne. While the synthetic scheme provides an easy way to prepare any combination of diacetylenic acids, the cost of the starting diacetylenic acid is high enough to prevent commercial use of the product diacetylenic acids.

The patented prior art preparation of the diacetylenic acids noted above, is further complicated by the fact that it is disadvantageous from commercial as well as product purity points of view. Preparation of the haloalkyne requires three steps, starting with an alkene, such as dodecene, progressing to an alkyne by the use of bromine and a basic ethanol, and finally arriving at the haloalkyne with the aid of the Grignard reagent and iodine. Similarly, it takes two steps to prepare an alkanoic acid, such as dodecanoic acid, starting either with an alkylenic acid, such as dodecylenic acid, or from a reaction of lithium acetylide/ethylene diamine complex with a bromoalkenoic acid, such as 9-bromododecanoic acid.

The overall yields for making a haloalkyne and an acetylenic acid are in the range of 60% and the reactions involve expensive and air sensitive reagents. Moreover, coupling a haloalkyne and an acetylenic acid is not only a low yield reaction of about 25% but also provides a mixture of three products. Though the separation of individual products is easy, additional reaction steps add to the product cost. The cost of the diacetylenics of interest herein is on the order $4,000/kg when prepared by the prior art process. There is a clear need for a new procedure which should be more cost effective and which minimizes the use of hazardous chemicals.

OBJECTS AND SUMMARY OF THE INVENTION

It is an object of this invention to prepare diacetylenics using a procedure that is more cost-effective and which minimizes the use of hazardous chemicals.

Another object of this invention is new compounds of diacetylenics containing at least one keto group.

Another object of this invention is new diacetylenic compounds containing at least one saturated or unsaturated cyclic group.

Another object of this invention is the preparation of diacetylenics which contain adjoining acetylene groups and carbon chains of varying length on either side thereof.

Another object of this invention is the ability to vary chain length on the sides of the adjoining acetylene groups in the diacetylenics described herein.

These and other objects of this invention are accomplished by oxidative coupling reaction involving an acetylenic acid to produce a diacetylenic diacid which is subsequently converted to a novel diacetylenic keto compound, which in turn is reduced to a reduced diacetylenic compound.

DETAILED DESCRIPTION OF THE INVENTION

This invention pertains to a high yield synthesis process, to diacetylenic compounds and to reduced diacetylenic compounds. More specifically, this invention pertains to a coupling process for making diacetylenics starting with an omega monoacetylenic acid, to diacetylenic compounds containing two adjacent acetylenic groups and to reduced diacetylenic compounds containing an alkyl or cyclic group at one or both ends thereof.

The versatile general procedure for making unsymmetric diacetylenics includes the steps of coupling an acetylenic acid using oxidative coupling involving cuprous chloride (CuCl), ethylamine ($EtNH_2$) and hydroxylamine hydrochloride ($NH_2OH.HCl$) to form a diacetylenic diacid followed by reaction of one of the carboxyl moieties on the diacetylenic diacid with a lithium reagent RLi wherein R is alkyl, phenyl or the like group to generate a keto derivative to form the diacetylenic keto acid. In the next reaction step, the keto group at one end of the diacetylenic keto acid is reduced using either hydrogenation with Raney nickel W-7 as catalyst or alkaline hydrazine hydrate or triethylsilane/trifluoroacetic acid reagent or some other keto reducing agent. The general procedure can be illustrated as follows:

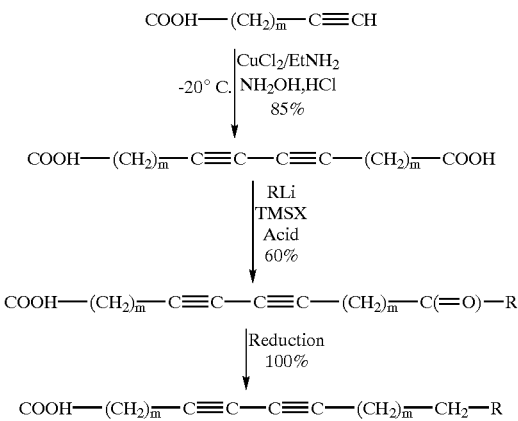

where m is 1–35, more typically 2–8 carbon atoms; and R is selected from alkyl groups of 1–10, more typically 1–6 carbon atoms, and cyclic groups containing 3–35 carbon atoms, more typically aromatic monocyclic and multicyclic groups containing 6–15 carbon atoms; and X is a halogen, typically chloride.

In the general procedure given above, if the acetylenic acid is solid, it is dissolved in water and then converted to a salt, typically a sodium or potassium salt. The acetylenic acid is then coupled to itself in the presence of cuprous chloride catalyst, which is unstable and facilitates the coupling reaction. In place of cuprous chloride, one can use pyridine, tetramethylethylene diamine, an aliphatic amine of 1–6 carbon atoms or another suitable catalyst. The coupling reaction is also carried out in the presence of basic ethylamine (EtNH$_2$), which dissolves and solubilizes cuprous chloride, and hydroxylamine hydrochloride (NH2 OH.HCl), which reduces any cupric chloride present as a result of conversion of cuprous chloride to cupric chloride (Cu$^{++}$ →Cu$^{+}$). The coupling reaction is typically carried out at room temperature although it can be accelerated at elevated temperatures. Elevated temperatures that degrade reactants or products should be avoided. The coupling reaction can be carried out at 0–40° C. and its duration is typically a minimum of about 2 hours and its termination can be confirmed by thin liquid chromatography (TLC). The coupling reaction is the first step in the process and its product is a symmetric diacetylenic dicarboxylic acid. Conversion of the coupling reaction is about 85%.

When cuprous chloride in ethylamine is added to the salt of the acetylenic acid, the reaction medium turns dark blue and several drops of hydroxylamine hydrochloride are added to the reaction medium to turn it light yellow temporarily since the reaction medium again turns dark blue. Addition of hydroxylamine hydrochloride is thus continued until the reaction medium remains yellow, indicating endpoint of the reaction step. Thin layer chromatography is typically used to confirm conversion of all acetylenic acid to the diacetylenic dicarboxylic acid.

In the next or the second step of the reaction, one or both of the carboxyl groups on the diacetylenic diacid are converted to a ketone by the lithium compound RLi where the R group is selected from alkyl and cyclic groups. The alkyl groups contain at least 1 carbon atom and typically up to about 6 carbon atoms whereas the aromatic groups are at least monocyclic containing at least 3 carbon atoms. The cyclic group can be a multicyclic, saturated or unsaturated group and can contain up to about 35, more typically up to about 14 carbon atoms. Typical alkyl groups suitable herein include methyl, ethyl, propyl, butyl and pentyl whereas typical aromatic groups contemplated herein include phenyl, naphthyl and biphenyl.

The lithium compound reacts with the two carboxylic groups and converts them to a first lithium salt in the following manner:

the carbonyl oxygen of which is next converted to a second lithium salt as follows:

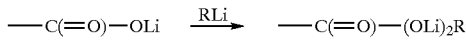

Reaction medium is cloudy when formation of the first lithium salt takes place and becomes pinkish when formation of the second lithium salt takes place.

The lithium compound, in ether or hexane or tetrahydrofuran or another suitable aprotic solvent, is added to the diacetylenic diacid and converts one or both carboxylic acid groups to mono or dilithium carboxylate, as demonstrated above. Subsequent reaction of lithium compound takes place on the oxygen in keto group, and the inorganic acid then hydrolyzes the second lithium salt to a keto group in the following manner:

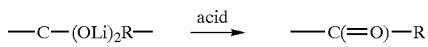

General procedure for making 2-keto-omega carboxylic acid is as follows: Dissolve 1.0 mmol diacetylenic dicarboxylic acid in 10 ml dry tetrahydrofuran. Purge the reaction flask with nitrogen and let the slow stream of nitrogen flow through the reaction medium. To the stirred solution, 3.3 mol equivalent of lithium reagent is added with the aid of syringe. Usually it takes 2 mol equivalents to react with two dicarboxylic acid and 1.3 mol equivalents lithium to react with each carbonyl group. At first, a white precipitate of lithium salt of carboxylic acid is produced at first. Further addition produces colored lithium alkoxy salt. After the reaction is considered over, usually in 2–3 hours, the excess of lithium reagent is quenched by addition of 3 mol equivalents of trimethylsilyl chloride. The reaction is then stirred for additional 30 minutes before quenching it with 10% sulfuric acid. The upper organic layer thus produced is separated by addition of additional diethyl ether. The combined ethereal extract is washed twice with distilled water. The ether extract is dried over anhydrous magnesium sulfate. Removal of the solvent provides crude product. The pure compound can be isolated by crystallization as well as by column chromatography over silica gel. To react carbonyl groups from both carboxylic acid groups, a 6 mol equivalent of lithium compound is used.

The acid hydrolysis is achieved with sufficient inorganic acid to make the reaction acidic. Although any inorganic acid can be used, hydrochloric or sulfuric acids have been found to be practical. Prior to acid addition, a small amount on the order of 1 mol equivalent to RLi of trimethylsilyl chloride (TMSC) is added to avoid a side hydrolysis reaction. Without trimethylsilyl chloride, typically get some alcohol whereas with it, the hydrolysis reaction is avoided and all of the carboxyl groups are converted to the keto group(s).

It should be apparent that the reaction with the lithium compound RLi can result in preparation of symmetrical and unsymmetrical diacetylenic compounds depending on how many carbons there are in the R group, what type of group the R group is, and whether one or both sides of the diacetylenic compound is provided with the keto group. This scheme represents that starting from an acetylene acid with "m" methylene units within its hydrocarbon chain, a diacetylenic acid can be produced in which the number of methylene units "n" in the methyl ending segment are always m≧1. Thus, starting with undecynoic acid with m=8, by reacting one end of a diacetylenic diacid with methyl lithium, ethyl lithium, propyl lithium, butyl lithium or pentyl lithium and then reducing the compound, one can produce acids with m=8 and n=9, 10, 11, 12 and 13 carbon atoms, as illustrated below:

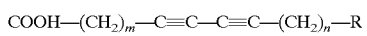

The second step of the reaction takes more than about 3 hours and up to about 5 hours, with the reaction phase with a lithium compound taking 3 or more hours, and the reaction phases with trimethylsilyl chloride and the inorganic acid taking a few minutes each. The endpoint of the second step of the process is typically determined with thin layer chromatography. Observation of a constant amount of the reactant or the product on thin layer chromatography plates indicates the completion of the reaction.

The diacetylenic keto compounds, i.e., the mono-keto and the di-keto diacetylenic compounds, also referred to herein as diacetylenic compounds, are novel and new compounds which can be used to make macrocyclics useful as pharmaceutical compounds.

The third step in the reaction is reduction of the keto group(s) in the manner shown:

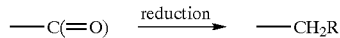

The reduction can be accomplished with Raney nickel, hydrazine hydrate/KOH reagent, or in any other suitable manner although the Raney nickel W-7 catalyst is typically used with an excess over the stoichiometric amount.

Synthesis of W-7 Raney nickel is well known. However, preparation of the catalyst is crucial for the reaction to proceed. The following method can be used in the preparation of catalyst. The W-7 Raney nickel reduction catalyst used herein was prepared by placing 600 ml of distilled water and 160 grams of sodium hydroxide pellets into a 2—liter Erlenmeyer flask equipped with a thermometer and a stirrer. The solution was stirred rapidly and allowed to cool to 50° C. in an ice bath. Then, 125 g of Raney nickel-aluminum alloy powder was added in small portions during a period of 25–30 minutes. The temperature was maintained at $50 \mp 2°$ C. by controlling the rate of addition of alloy to the sodium hydroxide solution and the addition of the ice to the cooling bath. When all of the alloy has been added, the suspension was digested at $50 \mp 2°$ C. for 50 minutes with gentle stirring. It was necessary to remove the ice bath and replace it with a hot-water bath to keep the temperature constant. After this period of digestion, the catalyst was washed with three 1-liter portions of distilled water by decantation. Catalyst was transferred to a 250—ml centrifuge tube or bottle with 95% ethanol, with centrifuging after each addition. In the same manner, the catalyst was washed three times with absolute ethanol and was stored in a refrigerator in a closed bottle filled with absolute ethanol.

If both ends of the diacetylenic keto compounds contain the carboxyl oxygen of a keto group, then amount of the Raney nickel catalyst will be about twice as much if only one end of the compounds contained the group. If the compound is diacetylenic keto acid, i.e., a compound containing a carbonyl oxygen in a keto group at only one end whereas there is a carboxy group at the other end of the compound, amount of the W-7 Raney nickel catalyst is typically 3–5 moles per 1 mole of the compound.

The endpoint of the third or the reduction step of the process is typically determined by taking an aliquot of the product mixture and running thin layer chromatography and NMR thereon to determine presence of the desired product.

Extraction of the product is typically made with a solvent, such as ether, and purification is achieved by column chromatography. Purity of the product of about 99% is typically achieved.

The reduction step typically takes several hours to complete, such as 3–8 hours.

The novel and new products produced in this manner are the following diacetylenic keto acids and ketones:

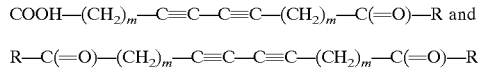

where m is typically 2–8 carbon atoms and R is typically a cyclic or a multicyclic group containing 3–35 carbon atoms, more typically an aromatic monocyclic or a multicyclic group containing 6–15. The above compounds with the R group selected from phenyl, biphenyl and naphthyl groups have been found to be of special interest because of their fluorescence which makes them especially useful as optical markers.

Having described the invention, the following examples are given as particular embodiments thereof and to demonstrate the practice and advantages thereof. It is understood that the examples are given by way of illustration an are not intended to limit the specification or the claims in any manner.

EXAMPLE 1

Synthesis of Docosa-10,12-diyn-1,20-dicarboxylic Acid

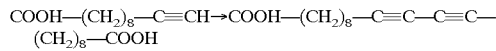

This material was synthesized by coupling undecynoic acid with the aid of cuprous chloride dissolved in 70% aqueous ethylamine. A 3.64 g. (20 mmol) undecynoic acid was dissolved in aqueous potassium hydroxide solution prepared by dissolving 2.2 g KOH in 15 mL water. To the stirred, foamy solution, 0.247 g (2.5 mmol) cuprous chloride dissolved in 10 mL of 70% ethylamine was added rapidly and the reaction was stirred efficiently. A yellow colored solution resulted, which turned blue over time. A few drops of 10% hydroxylamine hydrochloride were added to make the solution yellow, i.e., to convert cupric chloride to cuprous chloride.

The reaction mixture was left stirring overnight to assure completion of the reaction. Finally, the reaction was stopped by the addition of 15% by weight sulfuric acid in water. A fluffy white precipitate resulted, which was initially extracted with ether. Extraction with ether was not efficient since only an emulsion resulted. Therefore, the ether layer was removed and the solution was extracted with chloroform. In the beginning, heating of the reaction mixture was necessary to bring all the diacid into chloroform phase. Subsequent extractions were easy and extracted the remaining diacid. A solid powder was recovered by removal of the solvent and was treated with acetone, which left the diacetylenic diacid as white powder while dissolving most of the impurities mixed with the diacid to produce a brown solution. The solid dicarboxylic acid was recovered by filtration and washed with acetone to remove any adherent impurity. A 3.11 g acid was recovered, representing an 86% yield. A subsequent recovery step provided additional dicarboxylic acid, which improved the overall yield, which was not reported. NMR spectrum of the powder confirmed the identity of the compound. Chloroform: methanol (95%) solvent was used for developing TLC plates. Spot due to the diacetylenic dicarboxylic acid polymerized upon illuminating with UV light.

EXAMPLE 2

Synthesis of Docosa-10,12-diyn-1,20-dicarboxylic Acid

Accelerating the Rate of Reaction

This procedure is similar to that reported in previous example except that the reaction was carried out at 35° C.

and air was bubbled through the reaction mixture to accelerate the coupling reaction.

A 3.64 g. (20 mmol) undecynoic acid was dissolved in aqueous potassium hydroxide solution prepared by dissolving 2.2 g KOH in 15 mL water. To the stirred, foamy solution 0.247 g (20 mmol) cuprous chloride dissolved in 10 mL 70% ethylamine was added rapidly and the reaction was stirred efficiently. The reaction initiated very rapidly as indicated by the production of yellow color soon after mixing and the development of blue color in first few minutes. A few drops of 10% hydroxylamine hydrochloride were added to make the solution yellow, i.e., to convert cupric chloride to cuprous chloride. A yellow colored solution resulted, which turned blue over time. At this time, momentarily a slow stream of air was bubbled through the reaction to activate the catalyst by oxidizing it to cupric form. This step helped in coupling of the remaining acetylenic acid to diacetylenic dicarboxylic acid. Process continued till blue color ceased forming of its own after the addition of hydroxylamine hydrochloride. Total time taken for this process was about 30 minutes. The reaction was stopped by the addition of 15 % by weight sulfuric acid in water. A fluffy white precipitate resulted, which was extracted with chloroform by warming of the reaction mixture. In initial extraction warming was necessary to bring all the diacid into chloroform phase. Subsequent extractions were easy and extracted the remaining diacid. This provided 2.8 g diacetylenic dicarboxylic acid, i.e., a 77% yield. NMR showed the product to be 98% pure. About 2% impurity of undecylenic acid was removed by washing the acid with hot hexane (dicarboxylic acid insoluble in hexane). Additional batches indicated the acid might be synthesized in 86% or better yield.

EXAMPLE 3

Synthesis of 22-Oxotricosa-10, 12-diynoic Acid

Diacetylenic keto acid was prepared by selectively reacting 1.5M methyl lithium in diethyl ether with docosa-10,12diyn- 1,20-dioic acid at ice-water temperature. The reaction of MeLi with 22-oxotricosa-10, 12-diynoic acid, i.e., HOOC(CH$_2$)$_8$ C≡C—C≡C(CH$_2$)$_8$COOH, in ether was probed for its completion by taking a small aliquot, work up, and recording an NMR spectrum. Presence of starting material indicated that reaction didn't go through. This was due to partial insolubility of diacetylenic diacid in ether and more insolubility of Li carboxylate. Therefore, a small amount of the THF was added to make the diacid go into solution.

duced a purplish suspension. After stirring the reaction mixture at room temperature for 4 hours and usual work, the desired product was isolated in 86% yield. The product was characterized by proton and carbon NMR. In PMR a peak at 2.1 ppm indicated the presence of methyl group next to carbonyl. As shown in the preceding figure, chemical shifts due to methylene group alpha to carboxyl and diacetylenic groups were also observed to change.

EXAMPLE 4

Reaction of HOOC—(CH$_2$)$_8$—C≡C—C≡C—(CH$_2$)$_8$—COOH with Methyl Lithium 290 mg (0.8 mmol) of the dicarboxylic acid dissolved in 10 ml of tetrahydrofuran (THF) and 8 mL ether was reacted with 4.8 mmol (3.4 mL of 1.4 Molar solution) of methyl lithium (actual 6.72 mmol, 4.8 mL). At the end of addition, reaction mixture turned dark brown. After 2 hours, 0.5 mL trimethylsilyl chloride (2.68 mmol, 290 mg) was added which produced red turbid reaction mixture. Finally, the reaction was quenched with 10% aqueous sulfuric acid. Work up of the reaction provided 269 mg product, for a yield of 93 %. NMR spectrum indicated the absence of side product normally produced by addition of alkyl group from lithium reagent during hydrolysis.

EXAMPLE 5

Reaction of HOOC—(CH$_2$)$_8$—CCCC—(CH$_2$)$_8$—COOH with Butyl Lithium 200 mg (0.55 mmol) of the dicarboxylic acid dissolved in 10 ml THF was reacted with 3.2 mmol (2.0 mL of 1.6 Molar solution) of butyl lithium. At the end of addition reaction, the mixture instantaneously turned purple. After 1 hour of stirring the reaction mixture at room temperature 0.55 mL trimethylsilyl chloride (2.9 mmol, 313 mg) was added which produced red turbid reaction mixture. Finally, the reaction was quenched with 10% aqueous sulfuric acid. Work up of the reaction provided 212 mg crude product in 96% yield. NMR confirmed the molecular purity of the compound.

EXAMPLE 6

Reaction of HOOC—(CH$_2$)$_8$—C≡C—C≡C—(CH$_2$)$_8$—COOH with Phenyl Lithium 200 mg (0.55 mmol) of the dicarboxylic acid dissolved in 10 ml THF was reacted with 3.3 mmol (1.8 mL of 1.8 Molar solution) of phenyl lithium. Upon addition of each drop after

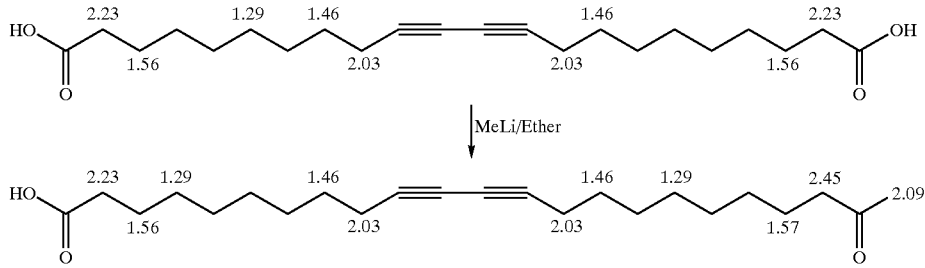

In this reaction, four to six mole equivalents of methyl lithium were used. Addition of first two moles produced thick white suspension and the third mole actually reacted with carboxylic oxygen and fourth mole was kept as an excess to let the reaction proceed further. The latter pro- 2 mol equivalents of reagent, the reaction mixture turned purple. After 1 hour of stirring at room temperature, 0.55 mL trimethylsilyl chloride (2.9 mmol, 313 mg) was added which produced red turbid reaction mixture. Finally, the reaction was quenched with 10% aqueous sulfuric acid. Work up of the reaction provided 188 mg product, for a yield of 81%. NMR of the crude revealed the presence of phenyl group as multiplet at 7.59 ppm containing an R group to form a diacetylenic compound whereby at least one end of the diacetylenic acid contains the R group and a —C(=O)—group, wherein the R group of

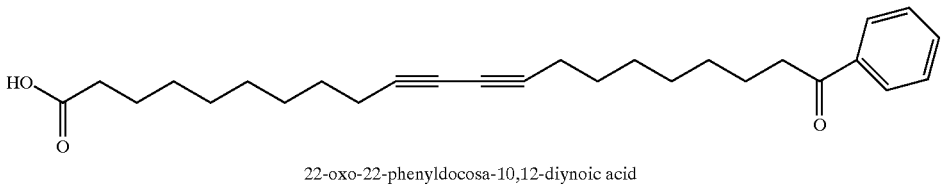

22-oxo-22-phenyldocosa-10,12-diynoic acid

EXAMPLE 7

Additional Example of the Synthesis of 22-Oxotricosa-10, 12-diynoic acid 1.08 g (3mmol) Icosa-9,11-diyne-1,20-dicarboxylic acid was suspended in 55 mL anhydrous THF and dissolved with slight warming. To this solution, 11.2 mL, 1.4 M methyl lithium in ether (8 mmol) was slowly added with the aid of syringe. A total of 2 mol equivalent of methyl lithium in ether were used per carboxylic acid to convert acid into ketone. The reaction turned into a viscous slurry from a free flowing suspension. The reaction was left stirring at room temperature overnight. The purplish colored suspension was treated with ice to quench the reaction. The product was extracted with ether, after acidifying the solution. The yellowish waxy product was characterized by NMR and found to contain the desired product as well as one byproduct tertiary alcohol due to additional reaction of methyl lithium present in the reaction mixture at the time of quenching. This problem was alleviated by addition of trimethyl silyl chloride in an amount enough to react with excess methyl lithium. This step provided clean reaction product.

EXAMPLE 8

Synthesis of Tricosa-10,12-diynoic Acid

The step used for converting keto to methylene group is a modified procedure previously reported by R. H. Mitchell and Y. Lai (Tetrahedron Letters, 21, 2637–38, 1980) for reducing ketones to methylene groups. Diacetylenic ketone, 57 mg (0.16 mmol) was gently heated in the presence of 3–5 mol excess of Ra—Ni (50 mg) in 50% ethanol for overnight. TLC showed a spot, which moved faster than the diacid. The reaction mixture was filtered through a cotton plug. Removal of the solvent under reduced pressure by repeated washing with chloroform afforded 58 mg crude product, a yield greater than 100% of diacetylenic acid. Removal of traces of solvent provided 50 mg diacetylenic acid, for a 90% yield.

While presently preferred embodiments have been shown of the novel process for making diacetylenic compounds and certain diacetylenic compounds, and of the several modifications discussed, persons skilled in this art will readily appreciate that various additional changes and modifications may be made without departing from the spirit of the invention as defined and differentiated by the following claims.

What is claimed is:

1. A process for preparing diacetylenic compounds comprising the steps of reacting an acetylenic acid in presence of a coupling catalyst to form a diacetylenic dicarboxylic acid and reacting the diacetylenic acid with a lithium compound containing an R group to form a diacetylenic compound whereby at least one end of the diacetylenic acid contains the R group and a —C(=O)—group, wherein the R group of the lithium compound is selected from the group consisting of hydrocarbon groups of 1–10 carbon atoms and cyclic group of 3–35 carbon atoms.

2. The process of claim 1 wherein the catalyst is selected from the group consisting of cuprous chloride, pyridine, tetramethylethylene diamine, aliphatic amines and mixtures thereof; wherein the acetylenic acid contains a carboxyl group at one end and an acetylenic group at the other end thereof; wherein the diacetylenic acid is characterized by adjacent acetylenic groups and a carboxyl group at least at one of the two ends thereof; and wherein the hydrocarbon groups of the lithium compound are alkyl groups which contain 1–6 carbon atoms and the cyclic groups are aromatic and contain 6–15 carbon groups.

3. The process of claim 2 which includes the step of reducing the diacetylenic compound whereby the —C(=O)— is converted to the —CH$_2$— group; wherein the catalyst is cuprous chloride; and wherein the diacetylenic acid has the following formula:

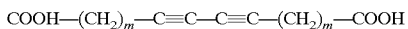

where m is 1–18.

4. The process of claim 3 wherein the cuprous chloride is in ethylamine in amount of from 0.2 mole to less than 1 mole of cuprous chloride per mole of the acetylenic acid and the process includes the steps of initiating the coupling reaction with oxygen and addition of hydroxylamine hydrochloride to convert dark reaction medium to light reaction medium during formation of the diacetylenic dicarboxylic acid.

5. The process of claim 4 wherein amount of the lithium compound is at least stoichiometric based on the diacetylenic acid, the diacetylenic compound has a structural formula selected from the group consisting of a) COOH—(CH$_2$)$_m$—C≡C—C≡C—(CH$_2$)$_m$—C(=O)—R, b) R—C(=O)—(CH$_2$)$_m$—C≡C—C≡C—(CH$_2$)$_m$—C(=O)—R, and c) mixtures thereof.

6. The process of claim 5 wherein the lithium compound has formula Rli and amount thereof is 3 mol equivalents to 6 mol equivalents based on the diacetylenic dicarboxylic acid and the process includes the step of reducing the diacetylenic compound to reduced diacetylenic compound.

7. The process of claim 6 wherein duration of said reacting step of the acetylenic acid is from about 10 minutes to about 12 hours; wherein duration of said reacting step of the diacetylenic acid is from about ½ hour to about 4 hours; and duration of said reduction step is from about 1 hour to about 5 hours.

8. The process of claim 7 wherein the alkyl groups in the lithium compound are selected from the group consisting of alkyl groups containing 2–6 carbon atoms; the aromatic groups in the lithium compound are selected from the group consisting of phenyl, naphthyl and biphenyl groups; and the reducing step is accomplished with Raney nickel.

9. The process of claim 8 including the steps of adding tetramethylsilyl halide and an inorganic acid during formation of the diacetylenic dicarboxylic acid whereby at least one end thereof contains the R group and a —C—(=O)— group.

10. The process of claim 9 wherein the trimethylsilyl halide is trimethylsilyl chloride and amount thereof per mole of the diacetylenic acid is 3 moles; and wherein the inorganic acid is selected from the group consisting of hydrochloric acid, sulfuric acid and mixtures.

11. A process for preparing a diacetylenic compound comprising the steps of reacting coupling an acetylenic acid in the presence of cuprous chloride to form the diacetylenic diacid having the formula COOH—(CH$_2$)$_m$—C≡C—C≡C—(CH$_2$)$_m$—COOH and then reacting the diacetylenic diacid with a lithium compound RLi to form the diacetylenic compound, the acetylenic acid is selected from the group consisting of compounds defined by the formula COOH—(CH$_2$)$_m$—C≡CH and mixtures thereof and the diacetylenic compound is selected from the group consisting of compounds defined by the formula COOH—(CH$_2$)$_m$—C≡C—C≡C—(CH$_2$)$_m$—C(=O)—R, R—C(=O)—(CH$_2$)$_m$—C≡C—C≡C—(CH$_2$)$_m$—C(=O)—R, and mixtures thereof, where m is 1–18 and R is selected from the group consisting of carbon groups containing 1–15 hydrocarbon atoms and aromatic monocyclic and multicyclic groups containing 6–35 carbon atoms.

12. The process of claim 11 wherein the cuprous chloride is in ethylamine and the process includes the steps of periodically adding hydroxylamine hydrochloride to convert dark reaction medium to light reaction medium during reaction of the acetylenic acid to form the diacetylenic diacid, adding triethylsilyl chloride and adding an inorganic acid during formation of the diacetylenic compound, the inorganic acid is selected from the group consisting of hydrochloric acid, sulfuric acid and mixtures thereof.

13. The process of claim 12 wherein the amount of cuprous chloride is from about 0.2 mole up to about 1 mole per mole of the acetylenic acid, the amount of ethylamine is at least sufficient to dissolve the solid cuprous chloride, the amount of hydroxylamine hydrochloride is sufficient to convert dark reaction mixture to light reaction mixture and keep it light during the coupling reaction of the acetylenic acid, and amount of RLi is 3 mol equivalent to 6 mol equivalent based on the diacetylenic dicarboxylic acid.

14. The process of claim 13 wherein the amount of trimethylsilyl chloride is equimolar to RLi and the amount of the inorganic acid is enough to make the solution acidic; and where m is 2–15 and R is selected from the group consisting of alkyl groups consisting of 2–6 carbon atoms, phenyl, naphthyl, biphenyl, anthracyl and mixtures thereof.

15. The process of claim 14 including the step of reducing the diacetylenic compound to a reduced diacetylenic compound selected from the group consisting of compound defined by the formula COOH—(CH$_2$)$_m$—C≡C—C≡C—(CH$_2$)$_m$—CH$_2$—R, R—CH$_2$—(CH$_2$)$_m$—C≡C—C≡C—(CH$_2$)$_m$—CH$_2$—R, and mixtures thereof, where m is 1–18 and R is selected from alkyl groups of 1–10 and cyclic groups containing 6–35 carbon atoms.

16. The process of claim 15 wherein the reducing step is carried out by a reducing agent selected from the group consisting of Raney nickel, triethylsilane/trifluoroacetic acid-boron trifluoride, And alkaline hydrazine hydrate, and mixtures thereof.

17. A composition of matter defined as follows:

COOH—(CH$_2$)$_m$—C≡C—C≡C—(CH$_2$)$_m$—C(=O)—R,

R—C(=O)—(CH$_2$)$_m$—C≡C—C≡C—(CH$_2$)$_m$—C(=O)—R, and mixtures thereof, where m is 1–18 and R is selected from alkyl groups of 1–10 and cyclic groups containing 3–35 carbon 5 atoms.

18. The composition of matter of claim 17 wherein m is 2–8 and R is selected from the group consisting of alkyl groups of 1–6 carbon atoms, aromatic groups of 6–15 carbon atoms and mixtures thereof.

19. A composition of matter defined as follows:

COOH—(CH$_2$)$_m$—C≡C—C≡C—(CH$_2$)$_m$—CH$_2$—R,

R—CH$_2$—(CH$_2$)$_m$—C≡C—C≡C—(CH$_2$)$_m$—CH$_2$—R, and mixtures thereof, where m is 1–18 and R is selected from alkyl groups of 1–10 and cyclic groups containing 6–35 carbon atoms.

20. The composition of matter of claim 19 wherein m is 2–15 and R is selected from the aryl groups consisting of phenyl, naphthyl, biphenyl, and anthracyl moieties.

* * * * *